United States Patent [19]

Stone

[11] Patent Number: 5,827,535
[45] Date of Patent: Oct. 27, 1998

[54] GRAPHICALLY IMPRESSED SOFTGEL AND METHOD FOR MAKING SAME

[75] Inventor: Dan D. Stone, Northridge, Calif.

[73] Assignee: Banner Pharmacaps, Inc., Chatsworth, Calif.

[21] Appl. No.: 667,189

[22] Filed: Jun. 21, 1996

[51] Int. Cl.⁶ ............................................. A61K 9/48
[52] U.S. Cl. ................................. 424/451; 424/456
[58] Field of Search ............................. 424/451, 456

[56] References Cited

U.S. PATENT DOCUMENTS

| | | | |
|---|---|---|---|
| D. 296,869 | 7/1988 | Bauwens | D9/302 |
| D. 312,209 | 11/1990 | Morrow et al. | D9/371 |
| D. 318,795 | 8/1991 | Christine | D9/302 |
| D. 326,410 | 5/1992 | Friedman | D9/517 |
| D. 327,008 | 6/1992 | Friedman | D9/521 |
| D. 327,216 | 6/1992 | Connell | D9/302 |
| D. 344,330 | 2/1994 | Schurig | D24/104 |
| D. 345,601 | 3/1994 | Schurig | D24/104 |
| D. 346,654 | 5/1994 | Bennell | D24/104 |
| D. 347,277 | 5/1994 | Snedden | D24/115 |
| D. 347,995 | 6/1994 | Schurig | D9/306 |
| D. 348,803 | 7/1994 | Bertolini | D9/302 |
| D. 350,690 | 9/1994 | Herro | D9/306 |
| D. 351,992 | 11/1994 | Jacques | D9/306 |
| D. 354,807 | 1/1995 | Bennell | D24/104 |
| 1,087,843 | 2/1914 | Smith . | |
| 3,395,202 | 7/1968 | Chu Yen | 264/132 |
| 3,413,396 | 11/1968 | Stearns | 264/132 |
| 3,436,453 | 4/1969 | Vincent, Jr. et al. | 424/6 |
| 4,720,378 | 1/1988 | Forse et al. | 424/6 |
| 5,002,775 | 3/1991 | Toya et al. | 424/467 |
| 5,009,894 | 4/1991 | Hsiao | 424/451 |
| 5,246,635 | 9/1993 | Ratko et al. | 264/4 |
| 5,270,054 | 12/1993 | Bertolini | 424/456 |
| 5,326,564 | 7/1994 | La Rosa et al. | 424/401 |
| 5,380,534 | 1/1995 | Schurig et al. | 424/456 |
| 5,405,642 | 4/1995 | Gilis et al. | 427/2.23 |
| 5,422,160 | 6/1995 | Ratko et al. | 428/141 |
| 5,484,598 | 1/1996 | Schurig et al. | 424/401 |

*Primary Examiner*—Thomas R. Weber
*Attorney, Agent, or Firm*—Jeffer, Mangels, Butler & Marmaro LLP

[57] ABSTRACT

A softgel includes a filled portion and a non-filled portion. At least one of the filled and non-filled portions has an external surface having defined thereon an impressed graphical representation.

12 Claims, 4 Drawing Sheets

GRAPHICALLY IMPRESSED SOFTGEL AND METHOD FOR MAKING SAME

FIELD OF THE INVENTION

The present invention relates to a softgel bearing an impressed graphic representation, for example a symbol such as a letter, a name, a logo, a pictorial representation and the like and to methods for making such a softgel.

BACKGROUND OF THE INVENTION

The need for encapsulation of liquids, semi-solids, and pastes within a gelatin shell in such a way as to preclude uncontrolled leakage has resulted in the development of a very fundamental dosage form: the soft gelatin capsule. The first version was developed in the middle of the 19th century. While an arduous and not particularly accurate process initially, current manufacturing processes are fully automated, with a high degree of precision.

The softgel (the currently accepted nomenclature adopted by the SoftGel Association) is a one-piece, hermetically sealed soft gelatin shell containing a fill, in particular a liquid, a suspension, or a semi-solid.

Softgels are presently manufactured in a variety of shapes, including spheres, ellipsoids, animals, etc. However, the presently known softgels are not themselves directly impressed with decorative or informational symbols or other graphical depictions.

A need exists for softgels which stably carry information, for example commercial information such as a product manufacturer or brand, or other graphical depictions. A need also exists for softgels which have a visually pleasing appearance.

SUMMARY OF THE PREFERRED EMBODIMENTS

According to one aspect of the present invention there is provided a softgel which includes a filled portion and a non-filled portion. At least one of the filled and non-filled portions has an external surface having defined thereon an impressed graphical representation. The impressed graphical representation can be letter, a number, a symbol, a logo or the like.

In a preferred embodiment, the non-filled portion bears the impressed graphical representation. Particularly preferably, the non-filled portion has opposed external surfaces, each of which bears an impressed graphical representation.

According to another aspect of the present invention there is provided a softgel which includes a filled portion, a non-filled portion, and an inner seal interposed between the filled portion and the non-filled portion. The non-filled portion has impressed thereon a graphical representation.

According to a further aspect of the present invention there is provided a softgel-forming die including a body having a surface, and outside land, a cavity, and a graphic land. The outside land is disposed on the surface of the body and encloses a portion of the surface of the body. The cavity is defined in the portion of the surface of the body enclosed by the outside land. The graphic land is disposed within the portion of the surface of the body enclosed by the outside land.

In a preferred embodiment, the graphic land is disposed adjacent the cavity. In another preferred embodiment, the graphic land is disposed within the cavity.

According to still another aspect of the invention, there is provided an apparatus for producing softgels as described herein. The apparatus includes supply means for providing first and second gelatin ribbons; injection means for providing a fill material to be encapsulated; and at least one softgel-forming die as described above.

Preferably, the apparatus includes two of the softgel-forming dies as described above. In an alternative embodiment, the apparatus includes one die as described above, and another die which does not include a graphic land.

According to still another aspect of the invention, there is provided a method for making a softgel having a filled portion and a non-filled portion. The method includes the steps of supplying first and second gelatin ribbons to an apparatus as described above; injecting a fill between the first and second ribbons; and sealing the first and second ribbons together to form the softgel, whereby a graphical representation is impressed on at least one of the filled and non-filled portions.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention can be made without departing from the spirit thereof, and the invention includes all such modifications.

DESCRIPTION OF THE FIGURES

The detailed description of the invention will be made with reference to the accompanying drawings, where like numerals designate corresponding parts of the figures. The drawings are meant to be generally illustrative of various examples of the present invention, but are merely examples and are not meant to be limiting of the scope of the invention.

DETAILED DESCRIPTION OF THE PREFERRED EMBODIMENTS

Figure 1:
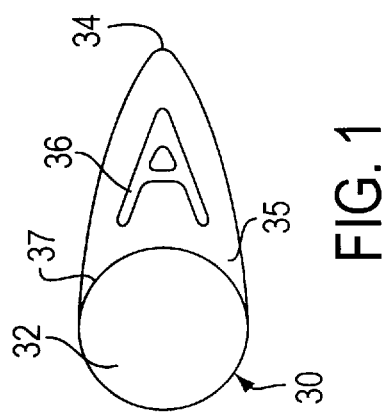
FIGS. 1–2 are top plan and side elevational views of a first embodiment of a softgel of the present invention.
Figure 2:
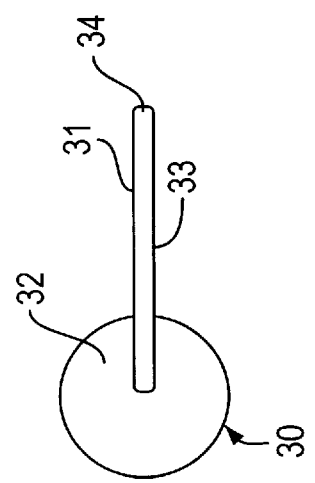

Turning now to the drawings, in FIGS. 1 and 2 a softgel 30 includes a filled portion 32, a non-filled portion 34, and an inner seal 37 disposed therebetween. Non-filled portion 34 has upper and lower surfaces 31 and 33. Upper and lower surfaces 31 and 33 have a non-graphically impressed portion 35 and an impressed graphical representation 36.

The filled portion 32 can be any shape formable by dies, particularly rotary dies. Such shapes can include, without limitation, triangles, hour-glass shapes, spheres, hearts, ellipsoids, etc., as well as combinations thereof.

Figure 3C:
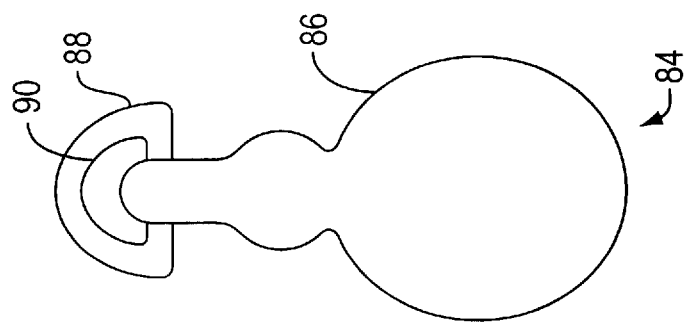
FIGS. 3A–C are top plan views of additional embodiments of softgels of the present invention.
Figure 3B:
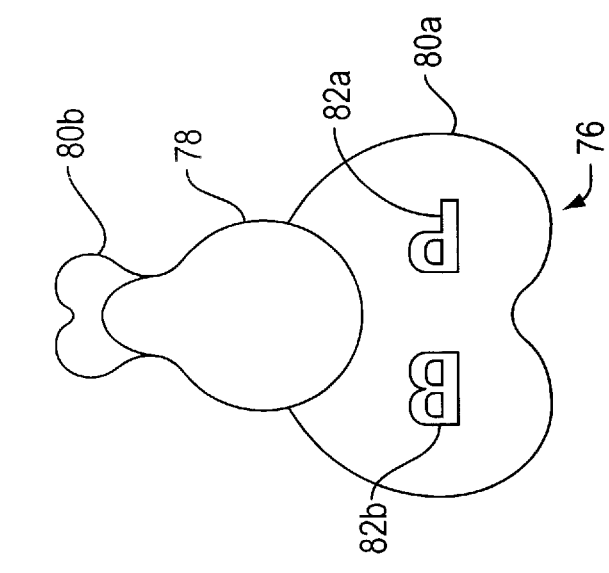
Figure 3A:
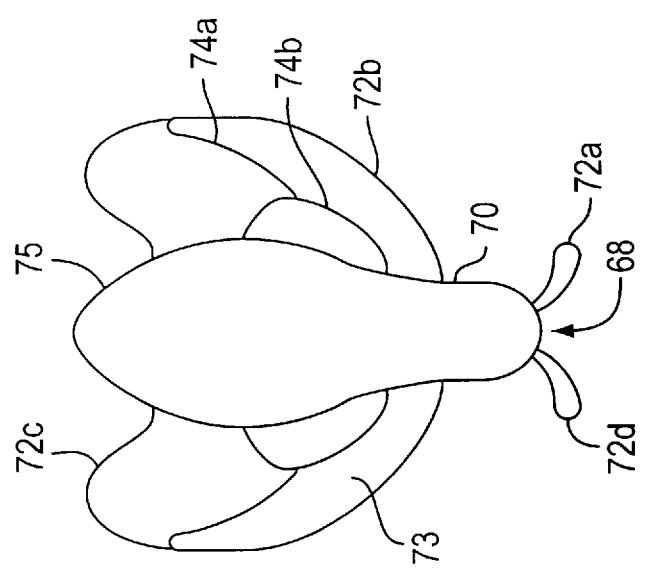

Non-filled portion 34 can protrude a selected distance from filled portion 32 of softgel 30. Non-filled portion 34 preferably has an external surface area which allows for the impressment of a graphical representation. The shape of non-filled portion 34 is determined by the shape of the die creating it. Therefore, any shape which the die can be configured to produce is a suitable shape. For example, FIG. 3A illustrates an insect- or bee-shaped softgel 68 having a filled portion 70, non-filled portions 72a–d, non-graphically impressed surface 73, and impressed graphical representations 74a–b. FIG. 3B illustrates a heart-shaped softgel 76 having a filled portion 78, non-filled portions 80a–b, and impressed graphical representations 82a–b. FIG. 3C illustrates a perfume bottle-shaped softgel 84 having a filled portion 86, a non-filled portion 88, and impressed graphical representation 90.

A single softgel 30 can include more than one non-filled portion 34. These non-filled portions 34 can be the same as or different from each other in size, shape and the nature of the graphical representation, if any, that is impressed thereon. For example, referring to FIG. 3A, the non-filled portions 34 can form the wings 72b and 72c and antennae 72a and 72d of an insect, such as a bee.

In a preferred embodiment the opposed upper and lower external surfaces 31 and 33 of a non-graphically impressed portion 35 of non-filled portion 34 are substantially parallel to each other. However, external surfaces 31 and 33 of non-filled portion 34 can vary by about ±15% due to, for example, variation in the thickness of the gelatin ribbon. The thickness of non-filled portion 34 typically is approximately equal to the combined thickness of the two gelatin ribbons being run through the dies. Such a thickness can occur when the relief portions 18 of the dies (see FIG. 4 and the discussion below) do not exert a compressive force on the ribbons. Alternatively, non-filled portion 34 can have a thickness from about 0.04 to about 0.09 inch. Preferably the thickness is from about 0.055 to about 0.075 inch. Most preferably, the thickness is about 0.06 inch.

Non-filled portion 34 preferably has a minimum surface area such that a graphical representation impressed thereon, or at least the shape of the non-filled portion 34 itself, can be recognized by the naked eye. In a preferred embodiment, the distance by which non-filled portion 34 protrudes from filled portion 32 is about 0.115 inch. If this distance is significantly less than 0.115 inch, it becomes more difficult to impress a graphical representation on non-filled portion 34.

The impressed graphical representation according to the invention can be in the form of a "positive" or a "negative" impression. That is, the impression formed on the selected external surface of the softgel can be an impression of the desired image (a "positive" representation) or an impression of the area surrounding the desired image, leaving an unimpressed portion of the softgel surface to form the actual representation (a "negative" representation). The latter impression affords a "raised" graphical representation.

The impressed graphical representation can be, for example, a letter or letters of any alphabet, including those letters which together form a word; a number or numbers; scientific, engineering or mathematical symbols; an advertising logo or logos; a pictorial representation of an object or objects; etc. Any combination of points, lines and open or closed curves representing an object, an idea or a concept, or a purely abstract rendition thereof, or any combination of any of the preceding can be formed. Specific examples can include, but are not limited to: the veined wings of an insect such as a bee or a butterfly (see FIG. 3A, 74a and 74b); letters (see FIG. 3B, 82a and 82b); a leaf vein pattern; a representation of the cap of a bottle (see FIG. 3C, 90); the ® symbol; an automotive logo; a human face; an animal; and the like.

In one embodiment graphical representations of varying depth can be placed one on top of another. For example, a first impressed graphical representation might be a geometric shape, such as a star. A second, deeper impressed graphical representation wholly or partially within the star might be a letter of an alphabet. Preferably, these impressed graphical representations of varying depth are produced through the use of a die which has graphic lands of correspondingly varying depth.

The formation of the impressed graphical representation preferably accompanies the fusion of the two ribbons forming the non-filled portion to each other. That is, the impression of the graphical representation on an external surface of the non-filled portion takes place as the two ribbons are fused, that is, melted together, or shortly before or after such fusion process takes place. The term "fusion" denotes a process wherein the two gelatin ribbons mingle together in a molten or fluid state under pressure exerted by application of a die.

In some embodiments, however, the impressed graphical representation is formed on only one of the two sides of softgel 30, with no fusion between the material forming the two sides of softgel 30 having occurred.

The impressed graphical representation can be formed on an external surface of the filled portion 32 of softgel 30 as well as, or in place of, non-filled portion 34.

First and second impressed graphical representations need not be identical. For example, the first impressed graphical representation can be the letter "A", and the second graphical representation can be a pictorial representation. Such embodiments are within the scope of the present invention. Additionally, the impressed graphical representations can be configured so that the same graphical representation can be impressed on both sides of the body of the softgel, but in different locations; a different graphical representation can be impressed on each side of the filled portion of the softgel; or two or more graphical representations the same as or different from each other can be impressed in any manner as described above.

An impressed graphical representation on a filled portion of a softgel according to the invention can be accomplished, for example, through the use of a hand held impressing device into which a softgel is placed, preferably while the material forming the softgel is still warm and malleable. Graphical impressions on non-filled portions of a softgel can similarly be formed.

Typically a graphical representation will be symmetrically disposed on each of two sides of the softgel, however, in particular embodiments this may not be necessarily so. Rather, the graphical representation can be impressed on only one side, the other side not being impressed. Alternatively, the same graphical representation can be impressed on both sides of the softgel, but in different locations. In other embodiments a different graphical representation can be impressed on each side. In another embodiment two or more graphical representations the same as or different from each other can be impressed in any manner as described above.

The graphical representations impressed on each external surface, for example 31 and 33, are preferably the same graphical representation in mirror-image correspondence.

That is to say the opposed external surfaces jointly form the obverse and reverse of a single pattern. However, other configurations as set forth in the specification are within the scope of the present invention.

The non-filled portion(s) of a softgel according to the invention preferably are free of visible internal voids. That is, in a preferred embodiment, the two gelatin ribbons forming the softgel are physically compressed together such that there is no gap(s) readily visible to the naked eye between them. In a particular embodiment this lack of visible gaps is due to the actual fusion of the two sides of the material forming the non-filled portion.

In other embodiments, the non-filled portion of the softgel can have one or more visible internal voids. Such an embodiment is formed when the two gelatin ribbons forming the softgel are not completely compressed together. Thus, one or more gaps remain between at least some portions of the two gelatin ribbons forming the non-filled portion of the softgel.

Referring again to FIGS. 1–2, an inner seal 37 is interposed between the filled portion 32 and non-filled portion 34. Inner seal 37 seals the two gelatin ribbons forming the softgel so that they meet and are fused with each other.

The inventive softgel preferably includes an external seal which functions to prevent leakage of material from the filled portion of the softgel to the exterior of the filled portion. One side of the external seal is in contact with the fill material, while the other side of the external seal is in contact with the external environment.

An example of this can be seen in FIG. 3A. The edges between the antennae 72a and 72d and the wings 72b and 72c of the bee and the area at the tail of the bee are defined by external seal 75.

The filled portion of the inventive softgel can include any suitable fill material, such as a liquid, a paste, a gel, a suspension, or even a granulated solid, tablet or caplet which can be injected or otherwise disposed within the filled portion of the softgel. Those of ordinary skill in the art can readily determine which formulations are suitable for softgel encapsulation.

Exemplary fills include but are not limited to the following: a fragrance such as a perfume, a cologne and the like (typically the amount of fragrance can range up to about 50 wt %. based on the total weight of the fill); a cosmetic, i.e., a composition applied to the skin to alter or improve the appearance of the skin, such as a blush, a foundation, and the like; a shaving composition, such as a shaving cream which can be applied to the skin to assist in the process of shaving hair from a human or animal; a hair care product to be applied to the hair of a person or animal suitable for washing hair, such as a shampoo, for conditioning hair, such as a conditioner, or for coloring hair, such as a dye; a skin care product formulation to be applied to the skin to, for example, cleanse, protect, moisturize, condition, soften, reduce wrinkles or otherwise treat the skin, such as soaps, body washes, moisturizers, sunscreens and alpha-hydroxy acid containing compositions; a foot care product such as a deodorizing composition or a fungal treatment, such as mycotin or other compositions generally applied to the feet; an eye care product; a paint, such as a paint suitable for inclusion in paint balls used in paint ball games; a vitamin; a drug; etc.

Particularly preferred fill materials include such pharmaceutically active compounds ("actives") as analgesics, anti-inflammatory agents, anti-pyretics, calcium channel blockers, beta-blockers, antibacterials, antidepressants, antidiabetics, anti-emetics, antihistamines, cerebral stimulants, sedatives, anti-parasitics, expectorants, diuretics, decongestants, antitussives, muscle relaxants, anti-Parkinsonian agents, broncholdilators, cardiotonics, antibiotics, antivirals, nutritional supplements (such as vitamins, minerals, fatty acids, amino acids, and the like), and mixtures thereof. Difficultly soluble pharmaceutical actives selected from the non-narcotic analgesics/non-steroidal anti-inflammatory drugs are especially useful.

Examples of preferred soluble pharmaceutical include, but are not limited to, ibuprofen, acetaminophen, acetylsalicylic acid, fenbuprofen, fenoprofen, flurbiprofen, indomethacin, ketoprofen, naproxen, their pharmaceutically acceptable salts, and mixtures thereof. Acetaminophen is especially preferred for use in these compositions.

Figure 7:
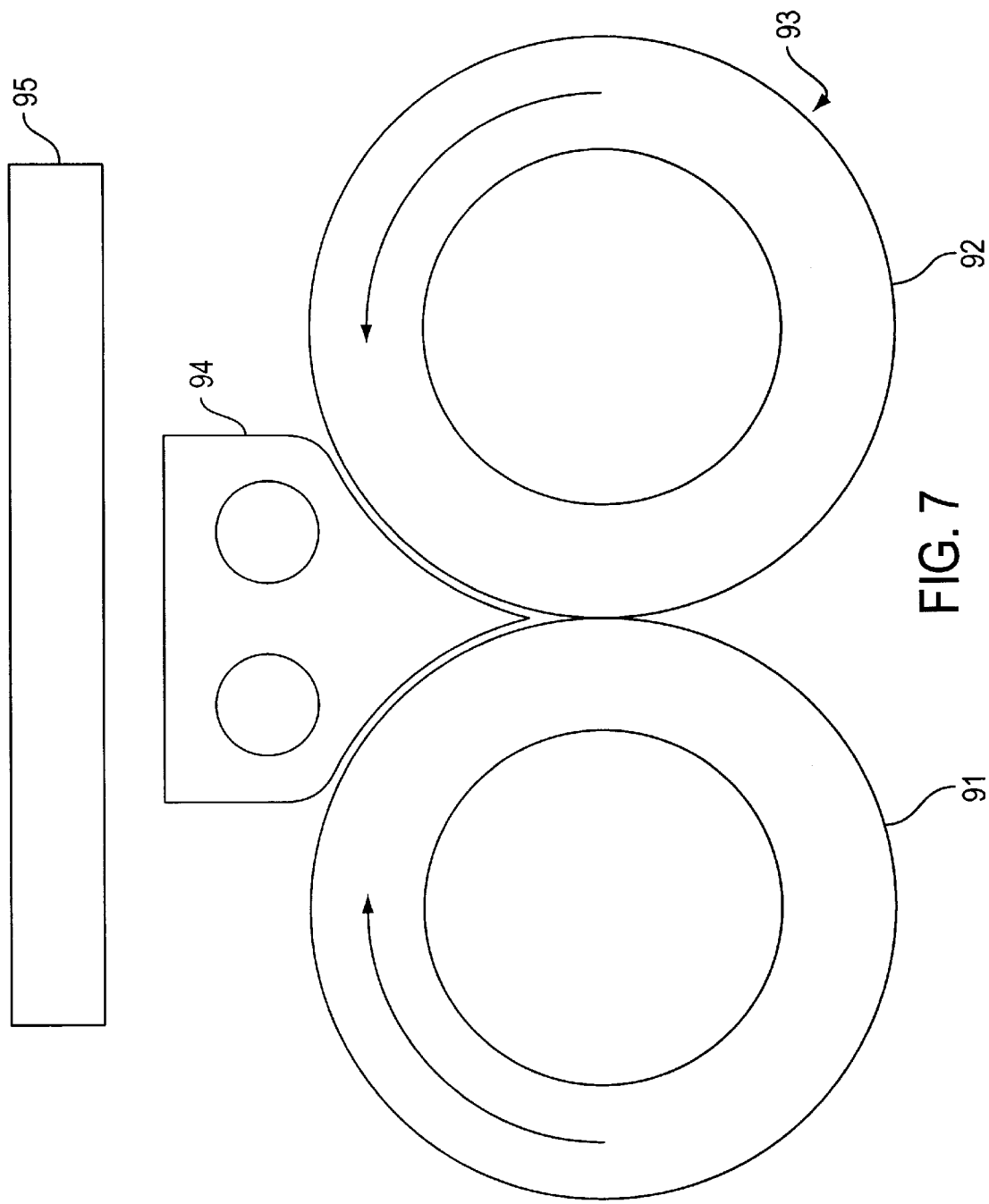
FIG. 7 is a side view of an apparatus which can be used in a process for producing impressed softgels according to the invention.

Turning now to FIG. 7, an apparatus 93 suitable for use in preparing softgels according to the invention includes a first die 91 and a second die 92. Injection means 94, as known to those of ordinary skill in the art, is used to inject a fill material to be encapsulated. Supply means 95, as known to those of ordinary skill in the art, is used to provide first and second gelatin ribbons. Preferably, first die body 91 and second die body 92 of apparatus 93 are symmetrically opposable.

Figure 4:
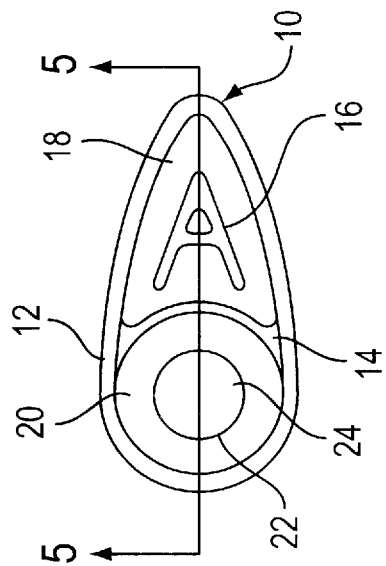
FIG. 4 is a top plan view of one particular embodiment of a portion of one half of a die of the present invention.
Figure 5:
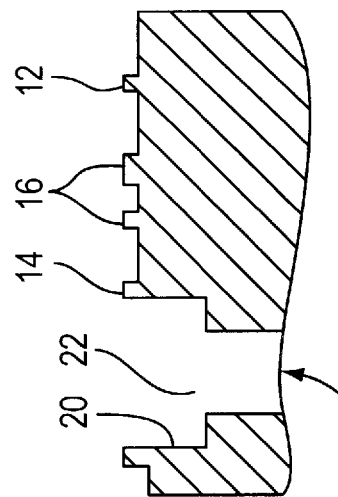
FIG. 5 is a side cross-sectional view along line A—A of the die embodiment of FIG. 4.

FIGS. 4 and 5 illustrate one embodiment of a portion of a die of the present invention. Die portion 10 includes outside land 12, inside land 14, graphic land 16, relief area 18, wall 20 of cavity 22, and vent hole 24. Knockout pins (not shown) which project through vent hole 24 can optionally be used to assist in clearing softgels from die portion 10, in manners known to those skilled in the art.

Figure 6:
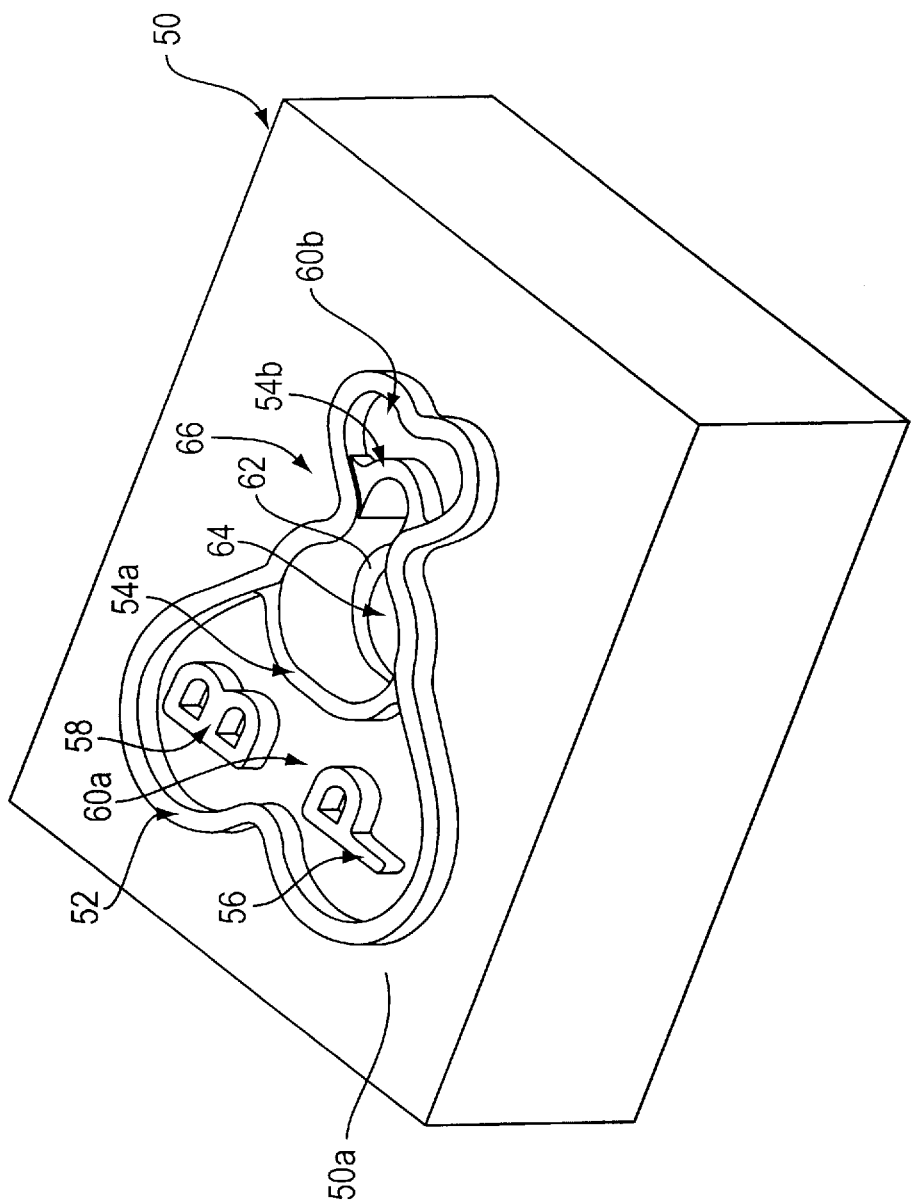
FIG. 6 is a perspective view of another embodiment of a portion of one half of a die of the present invention.

An alternative embodiment of a die according to the invention is shown in FIG. 6. Die 50 includes outside land 52, inside lands 54a and 54b, first graphic land 56, second graphic land 58, reliefs 60a and 60b, cavity 62, vent hole 64 and die body 66. Die 50 can be part of a twin rotary die and can therefore actually have a degree of curvature dependent upon the diameter of the rotary die body it is disposed upon.

Outside land 52, in conjunction with a matching land on a second, mirror-image die, seals the softgel fill portion and cuts the fill portion and non-fill portion out the gelatin ribbon, in a manner known to the art. The die lands are brought into contact typically through application of about 100 psi pressure. Inside lands 54a and 54b form an inner seal between the filled portion and a non-filled portion of the softgel.

Preferably, two of the foregoing dies are employed to produce softgels of the invention. The inside lands of each of the two dies preferably have heights relative to the heights of the outside lands thereof such that the inside lands are capable of sealing but not severing the gelatin ribbons passing between the dies. In specific exemplary embodiments, the inside lands preferably are about 0.001 to about 0.01 inch lower than the outside lands, more preferably about 0.005 to about 0.008 inch lower, very preferably about 0.0025 to about 0.0035 inch lower.

In FIG. 6, graphic lands 56 and 58 of die 50 function to impress the selected graphical representation onto the desired surface of the inventive softgel (here an external surface of a non-filled portion of the softgel).

In a particular embodiment, two dies having matched graphic lands are symmetrically opposable, in the sense that at least a part of one graphical land is opposable to at least a part of the second graphical land. However, the first and second graphic lands need not be identical. For example, the first graphic land could be the letter "A" and the second graphic land could be the letter "B", or another type of symbol such as a solid square opposed to the letter "A". Additionally, the graphic lands can be configured so that the same graphical representation can be impressed on both sides of, for example, a non-filled portion of the softgel, but in different locations; a different graphical representation can be impressed on each side of a non-filled portion of the softgel; or two or more graphical representations the same as or different from each other can be impressed in any manner as described above.

In a particular embodiment the graphic lands can be configured to contact each other and thereby cut out graphical representations, such that there is at least one void through the non-filled portion.

One or more reliefs (for example, reliefs 60a–b in FIG. 6) can be defined in die 50. Such a relief is a region bounded by an inside land, for example 54a and that part of the outside land 52 which at least partially delimits the non-filled portion of the softgel. Within the area of the relief, a graphic land (e.g., graphic land 58 of FIG. 6) can be located. Preferably, the height of the graphic land is less than the height of the outside land with respect to the base 50a of die 50.

In a preferred embodiment, the depth of the relief(s), if any, defined in die 50 is at least as great as the thickness of one of the gelatin ribbons from which the softgel is produced. In an alternative embodiment, the depth of the relief can be slightly less than the thickness of the gelatin ribbon. This results in a degree of compression of the gelatin ribbon.

According to a particular embodiment, the height of the outside land above the relief is at least about 0.025 inch, more preferably about 0.035 to about 0.04 inch.

The impressed graphical representation defined in the softgel of the present invention is readily distinguished from a depression or recession in an external surface of a non-filled portion of a softgel formed according to previously known processes. Such depressions or recessions are believed to result from the mere cohesive attraction of the gelatin ribbons toward each other, or from sagging of the gelatin ribbons under the influence of gravity, and are not formed by the application of an external force via a die as described herein. Such mechanisms are incapable of achieving the results of the present invention.

The most common modern manufacturing process involved in the preparation of softgels is a continuous method whereby two gelatin ribbons pass between twin rotating dies. As the ribbons meet, the liquid or other substance to be encapsulated is precisely injected between them. The capsule halves are sealed and ejected by the continuous rotation of the dies. See P. Tyle, *Specialized Drug Delivery Systems,* Marcel Dekker, Inc. (1990) for a general discussion of softgel manufacturing and production technology, in particular, Chapter 10 by Paul K. Wilkinson and Foo Song Hom, incorporated in their entirety herein by reference.

Various gelatin shell masses can be prepared, depending on the fill properties, climatic conditions, and end use. Typically gelatin formulations include the same basic ingredients, namely, gelatin, a plasticizer such as glycerin, water, and optionally preservatives. The formulations of gelatins are well known to those skilled in the art.

A typical gelatin shell formulation includes 47 wt % gelatin, 15 wt % glycerin (USP), and 38 wt % water, optionally with additional colorant materials. Other shell formulations can readily be prepared by one of ordinary skill in the art. Other formulations can also be employed, in particular the formulations described in application Ser. No. 08/482,170, now pending which is incorporated herein by reference.

Shell and fill formulations are discussed in Van Hostetler and J. Q. Bellard noted below, as well as in M. S. Paten, F. S. S. Morton and H. Seager, "Advances in Softgel Formulation Technology," *Manufacturing Chemists,* July 1989; William R. Ebert, "Soft Elastic Gelatin Capsules: A Unique Dosage Form," *Pharmaceutical Technology,* October 1977; H. Seager, "Soft gelatin capsules: a solution to many tableting problems," *Pharmaceutical Technology,* September 1985; U.S. Pat. Nos. 4,067,960 to Fadda; 4,198,391, to Grainger; 4,744,988, to Brox; and 4,780,316, to Brox. These references are incorporated in their entirety herein by this reference.

The softgels can be produced using known fills and shells by techniques known to those of skill in the art, for example, either the plate method or the continuous rotating die methods described previously.

The typical rotary die process, which generally requires a flowable liquid fill, but can utilize other fills such as a tablet or caplet, is readily adaptable to accommodate other fills such as those described above.

After the encapsulation and washing steps, the resulting capsules are typically dried in drying tunnels or rooms for about 3–7 days to remove water in the hygroscopic fill to about 6–10% by volume, preferably 8%. These are typically called "dry" capsules. The Karl Fischer test is used for determining water content. The drying occurs typically at about 21°–24° C. and at a relative humidity of 15–40%, preferably 15–30%. One can use infrared radiation to dry out the water as an alternative.

The amount of time the capsules are in the drying tunnels or room depends on the thickness of the gelatin shell, the amount of oil on the surface of the gelatin after the washing step, the density of capsules on the trays, and other factors known to those of ordinary skill in the art.

After the rotary die process is used to produce filled gelatin shells, the resulting capsules are typically washed with an evaporable solvent. Thereafter, the capsules are typically tumble dried in a series of hollow drums with perforated walls. Room air (25° C.) is continuously pumped through the rotating drums. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as discussed below. However, to avoid flat spots on the gels, drum drying preceding rack drying is preferred.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water can be removed from dry capsules by further heating, for example at 40° C., such a procedure has not been found to be practical or necessary. See Van Hostetler and J. Q. Bellard in *The Theory and Practice of Industrial Pharmacy,* "Capsules", (1970), Chapter 13, incorporated herein by reference, at pages 346–383, and in particular at page 380.

The drying time for most softgels is about 16–24 hours, but can be slightly longer if the softgels are over 20 minims in size or if the softgels contain a non-oily type liquid base. For smaller softgels, particularly those containing cosmetic compositions, the drying time can be about 4–6 hours. For other softgels containing, for example, shampoo compositions, the drying time can be about 48–72 hours.

Softgels permitted to come to water equilibrium in this controlled environment are considered "dry". After drying, the capsules are typically inspected and finished using varied known techniques.

While the description above refers to particular embodiments of the present invention, it will be understood that many modifications can be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A softgel comprising:
   a) a filled portion; and
   b) a non-filled portion, wherein at least one of said filled and non-filled portions has an external surface having defined thereon an impressed graphical representation.

2. The softgel of claim 1 wherein said non-filled portion has an external seal, and wherein said impressed graphical representation at least partially overlaps said seal.

3. The softgel of claim 1 wherein said non-filled portion has opposed external surfaces, each of said opposed external surfaces having defined thereon an impressed graphical representation.

4. The softgel of claim 1 wherein said impressed graphical representations defined on said opposed external surfaces jointly form the obverse and reverse of a single pattern.

5. The softgel of claim 1 wherein said filled portion has opposed external surfaces, each of said opposed external surfaces having defined thereon an impressed graphical representation.

6. The softgel of claim 1 further comprising a fill material selected from the group consisting of a fragrance, a cosmetic, a shaving composition, a hair care product, a skin care product, a foot care product, an eye care product, a vitamin, a drug and a paint.

7. A softgel comprising:
   a) a filled portion; and
   b) a non-filled portion, wherein at least one of said filled and non-filled portions has an external surface having defined thereon an impressed graphical representation which does not cover the entirety of said external surface.

8. A softgel comprising:
   a) a filled portion;
   b) a non-filled portion; and
   c) an inner seal interposed between said filled portion and said non-filled portion, wherein said non-filled portion has impressed thereon a graphical representation.

9. The softgel of claim 8 wherein said filled portion further includes an external seal.

10. The softgel of claim 8 further comprising a fill material selected from the group consisting of a fragrance, a cosmetic, a shaving composition, a hair care product, a skin care product, a foot care product, an eye care product, a vitamin, a drug and a paint.

11. The softgel of claim 8 wherein said non-filled portion is free of visible internal voids.

12. The softgel of claim 8 wherein said inner seal separates said fill material disposed in said filled portion from said non-filled portion.

* * * * *